United States Patent
Sultan

(10) Patent No.: US 6,679,832 B1
(45) Date of Patent: Jan. 20, 2004

(54) IMPLANTABLE DEVICE FOR TREATING IMPOTENCE BY DELIVERING A VASODILATOR AGENT TO THE ERECTILE BODIES OF THE PENIS

(76) Inventor: Hashem Sultan, 10939 SW. 149 Pl., Miami, FL (US) 33196

( * ) Notice: Subject to any disclaimer, the term of this patent is extended or adjusted under 35 U.S.C. 154(b) by 0 days.

(21) Appl. No.: 09/054,840

(22) Filed: Apr. 3, 1998

(51) Int. Cl.[7] .................................................. A61F 5/00
(52) U.S. Cl. ............................ 600/40; 600/38; 623/11
(58) Field of Search ........................ 623/11, 12, 11.11, 623/23.64; 600/38, 40; 128/898, 79

(56) References Cited

U.S. PATENT DOCUMENTS

| | | | |
|---|---|---|---|
| 3,731,681 A | | 5/1973 | Blackshear et al. |
| 3,853,122 A | * | 12/1974 | Strauch et al. ................ 600/40 |
| 4,013,074 A | | 3/1977 | Siposs |
| 4,572,168 A | | 2/1986 | Fischell |
| 4,604,994 A | * | 8/1986 | Sealfon ........................ 600/40 |
| 4,718,894 A | | 1/1988 | Lazorthes |
| 4,774,263 A | | 9/1988 | Dorman et al. |
| 4,813,951 A | | 3/1989 | Cannon |
| 4,828,544 A | * | 5/1989 | Lane et al. ..................... 604/9 |
| 4,941,461 A | | 7/1990 | Fischell |
| 4,958,630 A | * | 9/1990 | Rosenbluth et al. ......... 600/40 |
| 5,045,064 A | | 9/1991 | Idriss |
| 5,048,510 A | | 9/1991 | Hauschild et al. |
| 5,048,511 A | | 9/1991 | Rosenbluth et al. |
| 5,062,417 A | * | 11/1991 | Cowen ......................... 600/40 |
| 5,063,914 A | * | 11/1991 | Cowen ......................... 600/40 |
| 5,067,485 A | * | 11/1991 | Cowen ......................... 600/40 |
| 5,518,499 A | * | 5/1996 | Agar ............................ 600/40 |
| 5,851,176 A | * | 12/1998 | Willard ........................ 600/40 |

* cited by examiner

Primary Examiner—Corrine McDermott
Assistant Examiner—Kamrin Landrem
(74) Attorney, Agent, or Firm—Wood, Herron & Evans, LLP

(57) ABSTRACT

An implantable system for treating male impotence by delivering a vasodilator agent directly to the erectile bodies of the penis comprising an implantable supply pump; deformable reservoir; conducting catheter; and a dispensing catheter.

The supply pump is implanted into the abdominal wall. It includes a fluid chamber for holding a vasodilator substance and pressure chamber for exerting a pressure on a plate positioned between the two chambers for delivering the substance into a conducting catheter. The pressure chamber is either spring driven or driven by a liquid-vapor pressure reservoir.

The deformable reservoir is preferably implanted in the scrotum and being manually deformable for forcing the substance therefrom and into a dispensing catheter to the erectile bodies of the penis.

The dispensing catheter tip is preferably expandable and is operable to expand when the substance is forced into the catheter. The catheter tip includes plurality of openings for dispensing the substance therefrom into the erectile bodies.

18 Claims, 3 Drawing Sheets

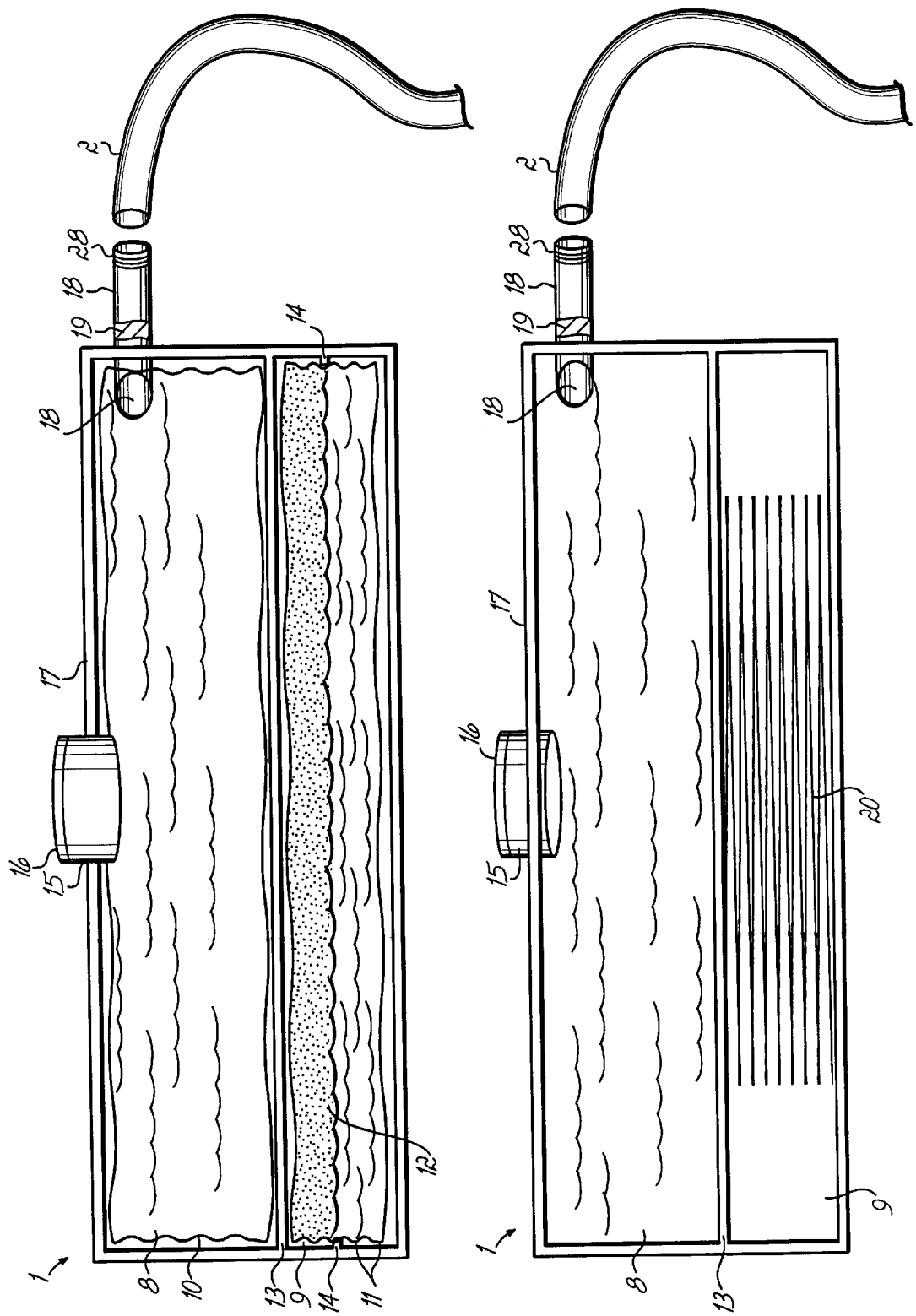

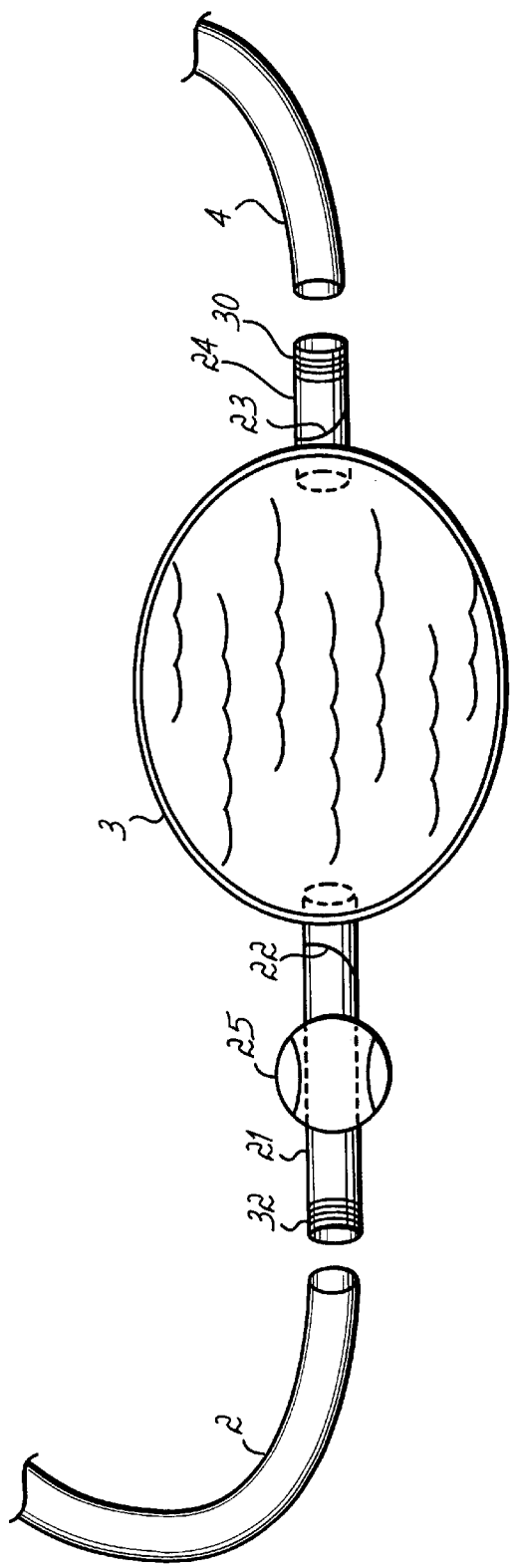
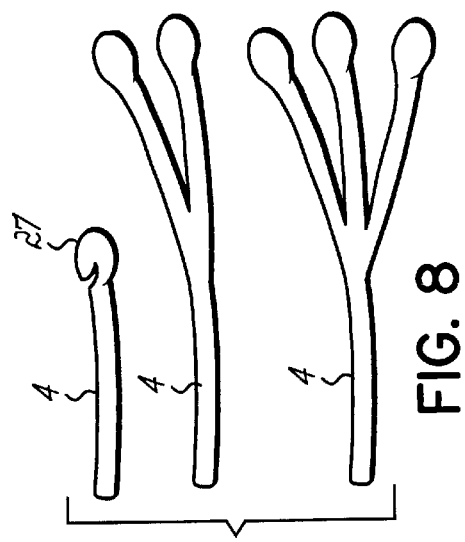
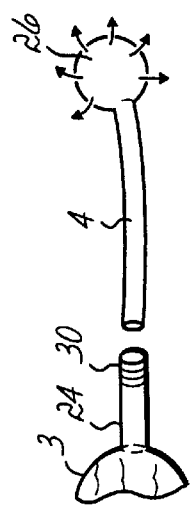

IMPLANTABLE DEVICE FOR TREATING IMPOTENCE BY DELIVERING A VASODILATOR AGENT TO THE ERECTILE BODIES OF THE PENIS

FIELD OF THE INVENTION

The present invention relates generally to implantable pumps and more particularly to a device and a method for stimulating penile erection by delivering a vasodilator agent into the penile corpus cavernosus via an implantable delivery line from an implantable pump.

BACKGROUND OF THE INVENTION

Impotence affects nearly ten million men in the United States alone. There are many causes for impotence in the human male, both pathological and psychological. Such impotence often destroys the male's psychological well being, and often seriously disrupts or even causes the dissolution of an otherwise fulfilling relationship.

The penis consists of the urethra and three erectile bodies (two corpora cavernosa and a corpus spongiosum. The smooth musculature of these erectile bodies and the smooth muscles of the arteriolar and arterial walls play a key role in the erectile process. In the flaccid state, these smooth muscles are tonically contracted by the sympathetic discharge, allowing only a small amount of arterial flow for nutritional purposes. The flaccid, penis is in a moderate state of contraction, as evidenced by further shrinkage in cold weather. Normally, sexual stimulation triggers the release of neurotransmitters from the cavernous nerve terminals.

This results in relaxation of these smooth muscles and the following events:

dilatation of the arterioles and the arteries by increased blood flow in both the diastolic and systolic phases;

trapping of the incoming blood by the expanding sinusoids (the spaces in between the smooth muscles of the erectile bodies);

compression of the subtunical venous plexus between the tunica albuginea (the fascia that surrounds the erectile bodies) and the peripheral sinusoids, reducing the venous outflow.

stretching of the tunica to its capacity, which encloses the emissary veins between the inner circular and the outer longitudinal layers and further decreases the venous outflow to a minimum;

an increase in intracavernous pressure (maintained at about 100 mm Hg), which raises the penis from the dependent position to the erect state (the full erection phase);

and a further pressure increase (to several hundreds millimeters of mercury)with contraction of the ischiocavernous muscles (rigid erection phase).

Erection thus involves sinusoidal relaxation, arterial dilatation, and venous compression. The importance of smooth muscle relaxation has been demonstrated in animal and human studies.

Several methods are being presently practiced to treat erectile dysfunction: oral agents; topical agents (transcutaneous and transurethral); hormones; vacuum therapy; intracavernous injection of vasodilator agents; and penile prosthesis. The results in all the above methods but the last two are very unsatisfactory. A recently introduced, March 1998, oral agent, VIAGRA, is claimed to have very good results, but with predictable side-effects due to systemic generalized vasodilatation, as this vasodilator agent is not specific for the penis. More clinical studies are still needed to prove its safety.

Intracavernous injection is the modem pharmacological treatment and consists of injecting a vasodilator agent into the corpus cavernosum of the penis, thus avoiding the undesirable systemic effect of the agent. The patient is taught how to perform the injection using a syringe and a needle under aseptic condition.

Erection after injection is achieved secondary to smooth muscle relaxation, resulting in increased blood flow to the erectile bodies. The quality of erection is very close to natural erection; it is warm and hard. A response rate of 80–100% has been achieved, depending on the underlying cause of impotence. However, many patients refuse this modality due to needle phobia and the stigma of carrying a needle and a syringe. Many patients also complain of the lack of spontaneity and interruption of foreplay associated with injecting the medicine.

Penile prosthesis gives good results. The quality of erection is excellent in terms of rigidity but the skin is cold. The implant has a high mechanical failure rate and serious complications and has the disadvantage of irreversibility. In addition, such implants involve gross insult to the normal anatomical structure of the penis.

In U.S. Pat. No. 5,518,499 of May 21, 1996, Agar describes a new device for implantation into the scrotum comprising a housing containing a vasoactive agent and a conduit communicably connected to the housing, and having a length such that when the housing is implanted in the scrotum, a terminal end of the conduit extends to a point in the corpus cavernosum.

Although his patent addresses the need for a device to deliver a vasoactive agent directly into the corpus cavernosum without the need for a syringe and a needle, the device suffers several disadvantages. The housing is filled, according to the description, only once before the incision is closed; the volume of the housing is limited because of its location in the scrotum. Even if the housing is meant to be refillable, there is no special sealing port for refilling; and the site of refilling (the scrotum) carries a higher risk of contamination and infection due to anatomical reasons (proximity to the anal orifice). There is only one terminal catheter into one of the corpus cavernosa. Despite the connection of the two corpus cavernosa, the vasoactive agent is not distributed equally in both corpora. There are are no other patents or articles that address the need for an implantable device that delivers a vasoactive agent internally to the corpus cavernosum.

Implantable pumps have been known for several decades to continuously deliver a selected medication to a certain location in the body in a scheduled or pre-programmed manner. An implantable infusion pump of this general type includes: an internal medication chamber or reservoir for receiving and storing a supply of the selected medication in liquid form; a pump mechanism; a refill port on the pump to permit transcutaneous needle access for purpose of periodically refilling the pump reservoir with a fresh supply of medication; and a catheter connecting the reservoir to the desired location.

Several methods have been described for the pump mechanism and the control of the rate of flow of the medication:

U.S. Pat. No. 3,731,681 describes an implantable infusion pump employing a liquid/vapor to provide a constant pressure for a drug flowing through a capillary tube in order to maintain a constant flow rate.

U.S. Pat. No. 4,772,263 describes an implantable infusion pump comprising a flexible spring diaphragm, which forms an outer back wall portion for housing of the infusion pump. The spring diaphragm applies a substantially constant force over a range of displacement and communicating body pressure to the drug chamber so as to maintain a uniform pressure between the drug chamber and the internal body pressure.

The pump also includes a capillary tubing, which serves as a flow-regulating resistance element or flow restrictor.

Several other pumps are already available in the market for different purposes using different driving forces, regulators, and electronic circuits to control the flow rate without any control by the patient and are inherently unresponsive to changing patient needs.

Few implantable devices are known wherein the patient himself manually actuates the pump in order to selectively deliver a dose from the implanted reservoir to the desired location.

U.S. Pat. No. 4,013,074 describes a device of this type which includes a peristaltic pump that can be manually activated through the skin by means of a suitable mechanical system.

U.S. Pat. No. 4,718,894 of Lazorthes describes a manually actuated implantable device with a manual pump located in the opposite zone of a flexible reservoir.

U.S. Pat. No. 4,813,951 of Cannon describes a pump apparatus, which includes a collapsible reservoir sac for holding fluids to be pumped, and a resilient pump chamber mechanism for withdrawing fluid from the reservoir and for supplying the fluid to a specific location within the body of the patient, but only when the patient manually applies forces to the implanted resilient chamber. The device also includes a windkessel device for extending the flow of the fluid for longer duration at steady flow rates.

None of the implantable pumps, particularly those with continuous flow, is suitable for use in impotency cases.

The present invention overcomes the shortcomings of the previous methods and devices for treating male impotence and provides the following advantages:

It provides a novel method and device for treatment of male impotence without the need for repeated penile needle stick, to achieve a natural physiological erection.

It is another object to overcome the above-described problems associated with the treating impotence.

It is another object of the invention to create a device with a relatively large reservoir that can provide an increased number of doses implanted in the abdominal wall.

It is another object of the invention to provide a deformable reservoir configured for implantation in the scrotum for dispensing its content to at least one erectile body of the penis, thus allowing easy and reliable use and capable to feed upon each actuation an exact and predetermined dose.

It is another object of the invention to provide a novel catheter tip which allows dispensing the medication from the said deformable reservoir to the erectile bodies without allowing the blood entering and thus blocking the catheter.

Other objects and advantages shall be understood and readily apparent to those skilled in the art upon reading the drawings, specifications and claims appended hereto.

SUMMARY OF THE INVENTION

An implantable system for treating male impotence by delivering a vasodilator agent directly to the erectile bodies of the penis comprises an implantable supply pump, deformable reservoir, conducting catheter, and a dispensing catheter. The supply pump is implanted into the abdominal wall. It includes a fluid chamber for holding a vasodilator substance and pressure chamber for exerting a pressure on a plate positioned between the two chambers for delivering the substance into a conducting catheter. The pressure chamber is either spring-driven or driven by a liquid-vapor pressure reservoir. The deformable reservoir is preferably implanted in the scrotum and is manually deformable for forcing the substance therefrom and into a dispensing catheter to the erectile bodies of the penis. The dispensing catheter tip is preferably expandable and is operable to expand when the substance is forced into the catheter. The catheter tip includes a plurality of openings for dispensing the substance therefrom into the erectile bodies.

The object of the present invention is to provide a novel method and device for treatment of male impotence, without the need for repeated penile needle stick, to achieve a natural physiological erection. It is another object to overcome the above-described problems associated with treating impotence. It is another object of the invention to create a device containing a relatively large reservoir that can provide an increased number of doses implanted in the abdominal wall. It is another object of the invention to provide a deformable reservoir configured for implantation in the scrotum for dispensing its content to the erectile bodies of the penis, thus allowing easy and reliable use and capability to feed upon each actuation an exact and predetermined dose.

BRIEF DESCRIPTION OF THE DRAWINGS

FIG. 4 is an illustration of the implantable supply pump with a liquid vapor pressure reservoir as a driving pressure chamber FIG. 5 is an illustration of a spring driven type of the implantable supply pump.

FIG. 6 is a cross sectional view of the manually deformable reservoir

FIGS. 7A and 7B are illustrations of the dispensing catheter with its tip in an inflation position (A), and the tip in the resting position (B).

FIG. 8 is an illustration of different variants of the dispensing catheter.

DETAILED DESCRIPTION OF A PREFERRED EMBODIMENT

Figure 1:
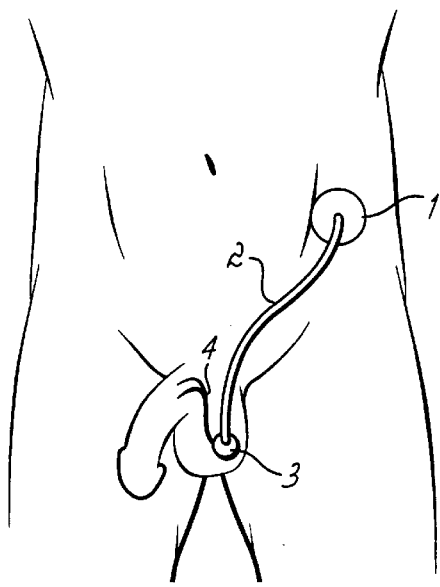
FIG. 1 is a general view of the device implanted in the abdominal wall scrotum, and penis
Figure 2:
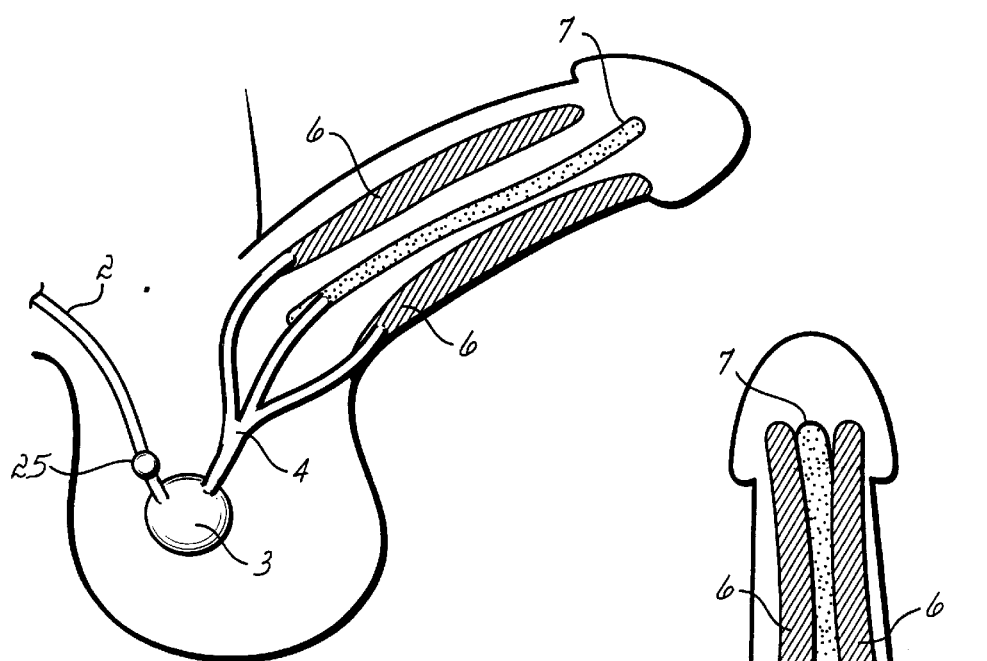
FIG. 2 is a sectional lateral view of the device implanted in the scrotum and the penis.
Figure 3:
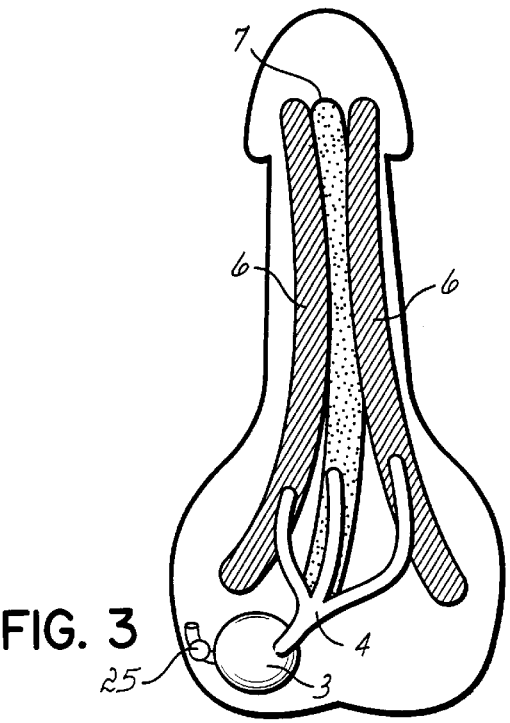
FIG. 3 is a sectional anterior view of the device implanted in the scrotum and the penis.

Referring to the drawings, FIGS. 1–3 illustrate a preferred embodiment of an implantable system for delivering a vasoactive substance to the three erectile bodies of the penis, namely the two corpus cavernosa 6 and the corpus spongiosus 7.

The system comprises four main parts:

1. an implantable supply pump 1 containing the vasoactive substance implanted in the anterolateral wall of the abdomen;

2. a deformable reservoir 3 implanted preferably in the scrotum and being manually deformable;
3. a delivery line, conducting catheter 2, connecting the supply pump to a deformable reservoir;
4. a dispensing catheter(s) 4 being coupled to said deformable reservoir for receiving a vasoactive substance from the reservoir and dispensing the substance to the erectile bodies of the penis (the two corpora cavernosa 6 and the corpus spongiosus 7).

As illustrated in FIGS. 4 and 5, the supply pump, being generally designated by the reference numeral 1, includes the standard features required of an implantable and refillable infusion pump constructed of nontoxic materials and compatible with both the drug solution and the body fluids. Titanium is a desirable material for forming a large portion of the housing 17, fittings, etc. The supply pump comprises a substantially sealed housing 17 encasing a medication fluid chamber 8 and an appropriate pump mechanism chamber 9 separated by a movable plate 13 positioned in between the two chambers.

The plate is preferably made of titanium or its alloy, and is about one to two millimeters thick with a shape identical to the shape of the horizontal cross-section of the housing which could be either circular, rectangular, etc. The diameter or length of the plate is one to two millimeters less than the housing cross-section to allow free movement of the plate. Alternatively, the plate can be made of the same diameter/length of the inner housing provided the edges of the plate moves freely on the inner wall of the housing with minimal friction.

The pressure chamber 9 is a variable volume reservoir and inversely proportional to the variable fluid chamber reservoir 8. As known in the art, the pressure chamber can be filled with either a liquid vapor pressure sack 11 or a spring 20. The preferred pressure fluid 12 comprises a fluorocarbon, Freon 113, which assumes a liquid-vapor state at normal body temperature.

The fluorocarbon is contained in a flexible and expansible sack 11. The sack is formed as a structural unit separate from the remaining component of the infusion pump, and is impermeable to fluorocarbon pressure fluids. A spacer 14 is made as a protrusion on the inner wall of the pressure chamber at a distance from the bottom of the chamber adequate to insure that at least a small portion of the pressure fluid remains in the vapor phase at all time.

The fluid (medication) chamber contains a fluid bag 10 constructed of nontoxic material, impermeable, compressible, and compatible with the medication in use. The bag can be constructed from polyurethane or silicon rubber, for example. The bag is in continuity with an inlet conduit 15. The upper end of the inlet conduit includes a self-sealing, penetrable member or septum 16 suitably positioned therein so as to provide a fluid type seal and yet provide for refilling of the bag by injection through the skin. The septum is slightly elevated or depressed from the surface of the housing for easy identification. The fluid bag is also continuous with an outlet conduit 18, which leads from the fluid chamber to the exterior of the housing. The fluid is driven out of the housing by the constant pressure from the pressure chamber and from the pumping mechanism induced by the patient when squeezing the deformable reservoir 3, as will be explained later. The outlet conduit contains a suitable filter 19 for filtering out bacteria and trapped gas which may be inadvertently introduced into the pump during the refilling process. The distal end of the outlet conduit is rigid and has a suitable connector 28 to connect to the conducting catheter 2.

FIG. 6 is an illustration of a sectional view of the deformable reservoir, being generally designated by the reference numeral 3. Its shape is preferably spherical (internal volume preferably one to two ml), and it is constructed of silicone rubber or polyurethane or other suitable material. It is preferably implanted in the scrotum where pinching it under the skin is feasible. However, it can be implanted anywhere under the skin where a rigid support is available (i.e., above the iliac crest bone under the skin where the reservoir can be compressed between the compressing finger and the bone).

The deformable reservoir has a conduit 21 with a suitable rigid connector 32 for connection to the conducting catheter 2. The conduit further comprises an inlet valve 22 to allow the fluid medication from the supply pump 1 through the conducting catheter 2 to the deformable reservoir 3 in one direction in that order and prevent the fluid from moving in the opposite direction. The valve is in the open position due to the pressure gradient between the supply pump 1 and the deformable reservoir 3. The valve preferably includes a hinged membrane spanning across the inlet opening, but any other form of unidirectional valve can be used like a ball and a socket, etc. The valve closes when the deformable reservoir is squeezed to effectively prevent the substance from traveling back to the pump from the reservoir.

The conduit 21 further comprises a supply valve 25 coupled to the delivery line (the conducting catheter 2 and the conduit 21). The supply valve is operable to close the delivery line when the fluid chamber is refilled to prevent the delivery of the substance to the reservoir. This is because the delivery line will be under high filling pressure. If the fluid is allowed to enter the reservoir under such a high pressure it will be undesirably forced into the penis through the dispensing catheter.

The supply valve is manually manipulative for closing when it is squeezed in the scrotum from the outside by the patient or the assistant helping the doctor refilling the pump supply. It has to be continuously squeezed during the filling procedure. When the filling is accomplished the valve is left alone to return to its normal open position by its elastic property. This supply valve is simply a thick elastic member, like silicon-rubber or a shape memory alloy (SMA), enclosing the distal part of the conduit 21, the preferred location, or any other part of the delivery line, preferably less than one centimeter in diameter.

The reservoir further comprises at least one outlet with at least one rigid conduit 24 with a suitable connector 30 for connection to the dispensing catheter(s) 4. The conduit 24 further comprises an outlet valve 23 to allow the fluid medication from the deformable reservoir to flow to the dispensing catheter 4 and prevent the fluid from moving in the opposite direction. The unidirectional valve is preferably a hinged membrane type, but any other types of unidirectional valves can be used.

As shown in FIGS. 2, 3, 7A and 7B, the dispensing catheter 4 is attached at its proximal end to outlet 30 and implanted into the erectile bodies at its distal end. The catheter is preferably greater than 14 gauge in diameter, less than four inches in length, and constructed of polyethylene, silicon-rubber, or any other suitable material. In the preferred embodiment of the device the dispensing catheter has one proximal stem which branches after a short distance into two or three branches, so that each branch will be implanted in each erectile body. However, several types of the dispensing catheter with one, two, or three ends can be provided and used according to the surgeon's preference.

In the preferred embodiment, the distal tip 26 of the dispensing catheter is constructed from a compliant elastic material, for example, rubber-silicon, which allows distention of the tip when the intraluminal pressure inside the catheter rises. The diameter of the catheter tip is preferably larger in diameter than the diameter of the rest of the catheter 4. This, according to Laplas Law, will allow easier inflation of the tip.

The catheter tip includes a plurality of openings for dispensing the medication into the erectile bodies of the penis. Those openings, at rest, are closed by the collapsing property of the tip and open only when the catheter tip expands in response to the medication being forced into the catheter by squeezing the deformable reservoir.

FIG. 8 shows different variant of the dispensing catheter tip, where the tip is provided with a one way valve 27 which opens when the deformable reservoir is squeezed, allowing the medication to flow out of the catheter into the penis, and closes when the intaluminal pressure of the dispensing catheter drops below a certain level. This will prevent blood and medication from returning back into the catheter.

FIG. 8 also illustrates some variations of the dispensing catheter with a plurality of dispensing tips for dispensing the medication into one, two, or three erectile bodies of the penis.

It is to be understood that the different parts of the device are provided with some supporting members (not shown in the drawings) for stitches to be secured in placed with the surrounding tissues.

The device is implanted in one simple surgical procedure and the pump supply is filled with the desired medication, preferably in a concentration that gives the appropriate dose needed for erection in 1 to 1.5 cc. When erection is desired, or when enhancement of an inadequate erection is desired, the patient has to squeeze the deformable reservoir with his finger. Although the fluid in the pump supply is under pressure, this pressure is less than the pressure necessary to overcome the opening pressure of the tip of the dispensing catheter. However, during refilling of the pump, the fluid pressure may increase to above the opening pressure of the tip of the dispensing catheter. Therefor, the said supply valve has to be squeezed during the refilling process by either the patient or the physician assistant.

Although an exemplary embodiment of the present invention has been shown and described, it will be apparent to those having ordinary skills in the art that a number of changes, modifications, improvements, or alterations to the invention as described herein may be made, none of which departs from the spirit of the present invention. Accordingly, no limitation on the invention is intended by way of the foregoing description and accompanying drawings, except as set forth in the appended claims.

What is claimed is:

1. An implantable system for delivering a vasodilator substance to the erectile bodies of the penis to treat male impotence comprising:

an implantable supply pump configured for implantation into a body at a position remote from the penis, the supply pump including a fluid chamber holding a vasodilator substance with an outlet therefrom and a pressure chamber to exert pressure on the fluid chamber to deliver a vasodilator substance from an outlet of the pump;

the supply pump including a refill inlet for refilling the fluid chamber;

an implantable deformable reservoir configured for implantation in the body proximate the penis, the deformable reservoir coupled to the outlet of said implantable pump through a delivery line for receiving the delivered substance;

a catheter configured for implantation into the penis and having a dispenser tip for dispensing a substance into the erectile bodies of the penis, the catheter being coupled to said deformable reservoir for receiving a substance from the reservoir and dispensing the substance to the erectile bodies of the penis;

the deformable reservoir being manually deformable for forcing the substance therefrom and into the catheter for dispensing the substance to the erectile bodies of the penis;

whereby a dosage of the substance may be selectively and repeatedly delivered to the erectile bodies of the penis when desired.

2. The system of claim 1 further comprising a plate positioned between said fluid chamber and said pressure chamber, the pressure chamber operable for exerting pressure on the plate for delivering the substance from the outlet.

3. The system of claim 1 further comprising an inlet valve coupled between the deformable reservoir and the outlet of said supply pump, the inlet valve operable for opening when the substance is delivered from the supply pump to the reservoir in a first direction and further operable for closing to effectively prevent the substance from travelling from the reservoir to the pump in a second direction.

4. The system of claim 3 wherein said inlet valve includes a hinged membrane spanning across an inlet opening into the reservoir, the membrane operable for hinging in a first direction to open the inlet opening when the substance is delivered to the reservoir and further operable to hinge in the second direction to close the inlet opening to effectively prevent the substance from traveling to the pump from the reservoir.

5. The system of claim 1 further comprising an outlet valve coupled between the deformable reservoir and the catheter, the outlet valve operable for opening when the substance is forced from the reservoir and into the catheter in a first direction and further operable for closing to effectively prevent the substance from travelling from the catheter to the reservoir in a second direction.

6. The system of claim 5 wherein said outlet valve includes a hinged membrane spanning across an inlet opening into the reservoir, the membrane operable for hinging in said first direction to open the inlet opening when the substance is delivered to the reservoir and further operable to hinge in the second direction to close the outlet opening to effectively prevent the substance from travelling back to the reservoir from the dispensing catheter.

7. The system of claim 1 wherein the catheter tip is expandable and is operable to expand when the substance is forced into the catheter.

8. The system of claim 1 wherein the catheter tip includes a plurality of openings for dispensing the substance therefrom.

9. The system of claim 1 wherein said catheter includes a plurality of dispenser tips for dispersing the substance into a plurality of erectile bodies of the penis.

10. The system of claim 1 further comprising a supply valve coupled to the delivery line, the supply valve being operable to close the delivery line when the fluid chamber is refilled to temporarily prevent the delivery of the substance to the reservoir.

11. The system of claim 10 wherein said supply valve is manually manipulatable for opening and closing the delivery line.

12. The system of claim 11 wherein said pressure chamber comprises an expansible sack, the sack filled with a liquid/vapor material to expand the sack and deliver the substance from the fluid chamber.

13. The system of claim 1 wherein said pressure chamber comprises a spring device, the spring device operable for exerting pressure on the fluid chamber.

14. A method for delivering a vasodilator substance to the erectile bodies of the penis to treat male impotence comprising:

implanting an implantable supply pump in a body at a position remote from the penis, the supply pump including a fluid chamber holding a vasodilator substance with an outlet therefrom and a pressure chamber to exert pressure on the fluid chamber to deliver a vasodilator substance from an outlet of the pump;

the supply pump including a refill inlet for refilling the fluid chamber;

implanting an implantable deformable reservoir in the body proximate the penis;

coupling the deformable reservoir to the outlet of said implantable pump through a delivery line for receiving the delivered substance;

implanting a catheter having a dispenser tip into the penis and positioning the dispenser tip into the erectile bodies of the penis for dispensing a substance into the erectile bodies;

coupling the catheter to said deformable reservoir for receiving a substance from the reservoir and dispensing the substance to the erectile bodies of the penis;

manually deforming the deformable reservoir for forcing the substance therefrom and into the catheter for dispensing the substance to the erectile bodies of the penis;

whereby a dosage of the substance may be selectively and repeatedly delivered to the erectile bodies of the penis when desired.

15. The method of claim 14 further comprising an inlet valve coupled between the deformable reservoir and the outlet of said supply pump, the inlet valve operable for opening when the substance is delivered from the supply pump to the reservoir in a first direction and further operable for closing to effectively prevent the substance from travelling from the reservoir to the pump in a second direction.

16. The method of claim 14 further comprising an outlet valve coupled between the deformable reservoir and the catheter, the outlet valve operable for opening when the substance is forced from the reservoir and into the catheter in a first direction and further operable for closing to effectively prevent the substance from travelling from the catheter to the reservoir in a second direction.

17. The method of claim 14 wherein the catheter tip is expandable and is operable to expand when the substance is forced into the catheter.

18. The method of claim 17 further including a supply valve coupled to the delivery line, the supply valve being operable to close the delivery line, the method further comprising the step of closing the supply valve when the fluid chamber is refilled to prevent the delivery of the substance to the reservoir.

* * * * *